United States Patent [19]

Gsell et al.

[11] 4,455,438
[45] Jun. 19, 1984

[54] CYCLOBUTANONE OXIMES

[75] Inventors: Laurenz Gsell, Basel; Jean-Claude Gehret, Aesch, both of Switzerland

[73] Assignee: Ciba-Geigy Corporation, Ardsley, N.Y.

[21] Appl. No.: 376,988

[22] Filed: May 10, 1982

Related U.S. Application Data

[62] Division of Ser. No. 252,527, Apr. 9, 1981, Pat. No. 4,348,414.

[30] Foreign Application Priority Data

Apr. 24, 1980 [CH] Switzerland .......................... 3170/80
Feb. 16, 1981 [CH] Switzerland .......................... 1007/81

[51] Int. Cl.³ .......................................... C07C 131/00
[52] U.S. Cl. .................................................. 564/253
[58] Field of Search ........................................ 564/253

[56] References Cited

PUBLICATIONS

Lautenschlaeger, F. et al., Can. J. Chem., vol. 41, (1963), pp. 863-875.

*Primary Examiner*—Glennon H. Hollrah
*Assistant Examiner*—L. Hendriksen
*Attorney, Agent, or Firm*—Frederick H. Rabin

[57] ABSTRACT

Cyclobutanone oxime carbamates of the formula

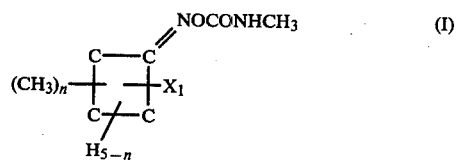

wherein n is 1 to 5 and $X_1$ is hydrogen, halogen, $C_1$-$C_4$alkoxy or $C_1$-$C_4$alkylthio. A process for obtaining the compounds of the formula I and their use in pest control as well as the cyclobutanone oximes used as intermediates are described.

8 Claims, No Drawings

CYCLOBUTANONE OXIMES

This is a division of application Ser. No. 252,527 filed on Apr. 9, 1981, now U.S. Pat. No. 4,348,414.

The present invention relates to cyclobutanone oxime carbamates, to the production thereof and to the use thereof in pest control, as well as to the cyclobutanone oximes employed as intermediates.

The cyclobutanone oxime carbamates have the formula

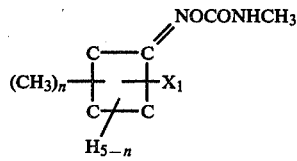

wherein n is 1 to 5 and $X_1$ is hydrogen, halogen, $C_1$-$C_4$alkoxy or $C_1$-$C_4$alkylthio.

Halogen in the above definition denotes fluorine, chlorine, bromine or iodine, with chlorine being preferred.

Alkoxy and alkylthio groups $X_1$ can be straight-chain or branched. Examples of such groups comprise: methoxy, methylthio, ethoxy, ethylthio, propoxy, propylthio, isopropoxy, isopropylthio, n-butoxy, n-butylthio.

Preferred compounds on account of their activity are those of the formula I, wherein n is 1 to 4 and $X_1$ is hydrogen, chlorine, methoxy, ethoxy or methylthio.

Particularly preferred compounds, however, are those of the formula II

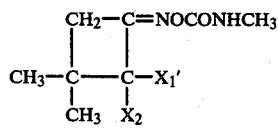

wherein $X_1'$ is hydrogen, chlorine or methylthio, and $X_2$ is hydrogen or methyl.

The compounds of the formula I can be obtained by the following known method:

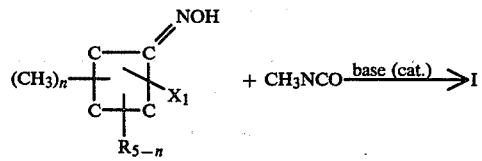

In formula III, n and $X_1$ are as defined for formula I. Suitable bases for this process are, in particular, tertiary amines such as trialkylamines, dialkyl anilines and pyridines.

The compounds of the formulae I to III can be in the form of different stereoisomers. Accordingly, the compounds of the formulae I, II and III will be understood as comprising both individual stereoisomers as well as mixtures of stereoisomers.

The process is carried out under normal pressure in a temperature range from −25° to 150° C., preferably from 0° to 100° C., and in a solvent or diluent.

Examples of suitable solvents or diluents are: ethers and ethereal compounds such as diethyl ether, diisopropyl ether, dioxane or tetrahydrofurane; aromatic hydrocarbons such as benzene, toluene and xylenes; ketones such as acetone, methyl ethyl ketone or cyclohexanone; nitriles such as acetonitrile; esters such as ethyl acetate or butyl acetate; as well as dimethyl formamide, dimethyl sulfoxide and halogenated hydrocarbons. The starting materials of the formula III are novel, but can be prepared by known methods (cf. Example 1).

The compounds of the formula I are suitable for controlling pests of animals and plants. They have e.g. an advantageous action against phytopathogenic microorganisms and nematodes. In particular, however, the compounds of the formula I are suitable for controlling all development stages of insects, for example of the order Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and also mites and ticks of the order Acarina.

Most particularly, the compounds of the formula I are suitable for controlling plant-destructive insects, especially feeding insects and sucking insects, in ornamentals and crops of useful plants, particularly in cotton (e.g. *Anthonomus grandis*) and vegetables (e.g. *Leptinotarsa decemlineata*, *Aphis craccivora* and *Myzus persicae*). In addition, the compounds of the formula I have a broad ovicidal and ovilarvicidal action.

The compounds of the formula I are used in unmodified form or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. The methods of application, such as spraying, atomising, dusting, scattering or pouring, are chosen in accordance with the intended objectives and the prevailing circumstances, just like the nature of the compositions.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surfactants.

Suitable solvents are: aromatic hydrocarbons, preferably the fractions containing 7 to 12 carbon atoms, e.g. toluene, xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the polarity of the active ingredient of the formula I to be formulated, suitable surface-active compounds are nonionic, cationic and/or anionic surfactants having good emulsifying, dispersing and wetting properties. The term "surfactants" will also be understood as comprising surfactant mixtures.

Suitable anionic surfactants can be both water-soluble soaps and water-soluble synthetic surface-active compounds.

Suitable soaps are the alkali, alkaline earth or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali, alkaline earth or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonyphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylene-diaminopropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol-polyethoxyethanols, castor oil polyglycol ethers, polypropylene/polyoxyethylene adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ringwood, N.J., 1979.

The pesticidal formulations usually contain 0.1 to 99%, preferably 0.1 to 95%, of a compound of the formula I, 1 to 99% of a solid or liquid adjuvant, and 0 to 25%, preferably 0.1 to 25%, of a surfactant.

Whereas commercial products are preferably formulated as concentrates, the end user will normally employ dilute formulations.

The formulations can also contain further additives such as stabilisers, antifoams, viscosity regulators, binders, adhesives, as well as fertilisers, in order to attain special effects.

The compounds (active ingredients) of the formula I can be formulated e.g. as follows (throughout, percentages are by weight):

| Formulation Examples for liquid active ingredients of the formula I | |
|---|---|
| 1. Emulsifiable concentrates | |
| (a) active ingredient | 20% |
| calcium dodecylbenzenesulfonate | 5% |
| castor oil polyethylene glycol ether (36 moles of ethylene oxide) | 5% |
| xylene mixture | 70%; |
| (b) active ingredient | 40% |
| calcium dodecylbenzenesulfonate | 8% |
| tributylphenol polyethylene glycol ether (30 moles of ethylene oxide) | 12% |
| cyclohexanone | 15% |
| xylene mixture | 25%; |
| (c) active ingredient | 50% |
| tributylphenol polyethylene glycol ether | 4.2% |
| calcium dodecylbenzenesulfonate | 5.8% |
| cyclohexanone | 20% |
| xylene mixture | 20%. |

Emulsions of any required concentration can be produced from such concentrates by dilution with water.

| 2. Solutions | |
|---|---|
| (a) active ingredient | 80% |
| ethylene glycol monomethyl ether | 20%; |
| (b) active ingredient | 10% |
| polyethylene glycol 400 | 70% |
| N—methyl-2-pyrrolidone | 20%; |
| (c) active ingredient | 5% |
| epoxidised vegetable oil | 1% |
| ligroin (boiling range 160–190° C.) | 94%; |
| (d) active ingredient | 95% |
| epoxidised vegetable oil | 5%. |

These solutions are suitable for application in the form of microdrops.

| 3. Granulates | |
|---|---|
| (a) active ingredient | 5% |
| kaolin | 94% |
| highly dispersed silicic acid | 1% |
| (b) active ingredient | 10% |

3. Granulates

| | |
|---|---|
| attapulgite | 90%. |

The active ingredient is dissolved in methylene chloride, the solution is sprayed onto the carrier, and the solvent is subsequently evaporated off in vacuo.

4. Dusts

| | | |
|---|---|---|
| (a) | active ingredient | 2% |
| | highly dispersed silicic acid | 1% |
| | talcum | 97% |
| (b) | active ingredient | 5% |
| | highly dispersed silicic acid | 5% |
| | kaolin | 90%. |

Dusts which are ready for use are obtained by intimately mixing the carriers with the active ingredient.

Formulation examples for solid active ingredients of the formula I

5. Wettable powders

| | | |
|---|---|---|
| (a) | active ingredient | 20% |
| | sodium lignosulfonate | 5% |
| | sodium laurylsulfate | 3% |
| | highly dispersed silicic acid | 5% |
| | kaolin | 67% |
| (b) | active ingredient | 60% |
| | sodium lignosulfonate | 5% |
| | sodium diisobutylnaphthalene-sulfonate | 6% |
| | octylphenol polyethylene glycol ether (7–8 moles of ethylene oxide) | 2% |
| | highly dispersed silicic acid | 27%. |

The active ingredient is thoroughly mixed with the adjuvants and the mixture is thoroughly ground in a suitable mill, affording wettable powders which can be diluted with water to give suspensions of the desired concentration.

6. Emulsifiable concentrate

| | |
|---|---|
| active ingredient | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50%. |

Emulsions of any required concentration can be obtained from this concentrate by dilution with water.

7. Dusts

| | | |
|---|---|---|
| (a) | active ingredient | 5% |
| | talcum | 95% |
| (b) | active ingredient | 8% |
| | kaolin | 92%. |

Dusts which are ready for use are obtained by mixing the active ingredient with the carriers, and grinding the mixture in a suitable mill.

8. Extruder granulate

| | |
|---|---|
| active ingredient | 10% |
| sodium lignosulfonate | 2% |
| carboxymethylcellulose | 1% |
| kaolin | 87%. |

The active ingredient is mixed and ground with the adjuvants, and the mixture is subsequently moistened with water. The mixture is extruded and then dried in a stream of air.

9. Coated granulate

| | |
|---|---|
| active ingredient | 3% |
| polyethylene glycol 200 | 3% |
| kaolin | 94%. |

The finely ground active ingredient is uniformly applied, in a mixer, to the kaolin moistened with polyethylene glycol. Non-dusty coated granulates are obtained in this manner.

10. Suspension concentrate

| | |
|---|---|
| active ingredient | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32%. |

The finely ground active ingredient is intimately mixed with the adjuvants, giving a suspension concentrate from which suspensions of any desired concentration can be obtained by dilution with water.

Example 1: Preparation of 2-methylthio-3,3-dimethylcyclobutanone-oxime-N-methylcarbamate (a) Preparation of 2-chloro-3-dimethylcyclobutanone oxime:

A solution of 38.2 g of hydroxylamine hydrochloride in 150 ml of hot methanol is added to a solution of 33 g of 85% potassium hydroxide in 75 ml of hot methanol. The mixture is cooled and the potassium chloride is removed by filtration and 66.25 g of 2-chloro-3-dimethylbutanone are then added dropwise at 10°–25° C. After 2 hours the solvent is evaporated and the residue is recrystallised from methylene chloride/hexane (1:1), affording the compound of the formula

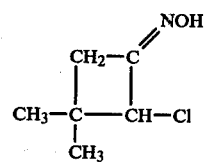

with a melting point of 64°–68° C.

The following oximes are prepared in similar manner:

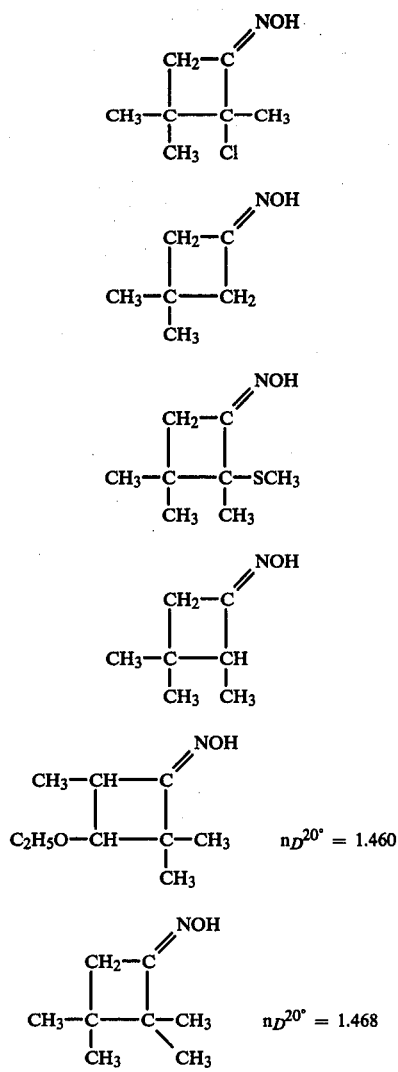

(b) Preparation of 2-methylthio-3,3-dimethylcyclobutanone oxime:

5.6 g of methylmercaptan are introduced at −10° C. into a solution of 5.7 g of sodium methylate in 100 ml of methanol and then a solution of 15.7 g of 2-chloro-3-dimethylcyclobutanone oxime in 50 ml of methanol is added dropwise at 0° C. The mixture is stirred for 3 hours and the precipitated salt is isolated by filtration, a portion of the methanol is evaporated off and 100 ml of water are added. After extraction with 100 ml of methylene chloride the methylene chloride phase is washed with water, dried over sodium sulfate and concentrated. The crude product is purified by chromatography with ether/hexane (1:1) as eluant, affording the compound of the formula

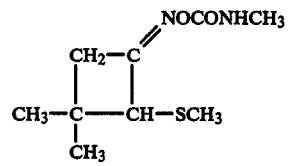

which can be reacted to the oxime carbamate without further purification.

(c) Preparation of the final product:

4.5 g of methyl isocyanate and 3 drops of triethylamine are added at 20° C. to 9.6 g of crude 2-methylthio-3,3-dimethylbutanone oxime in 100 ml of acetone. The reaction mixture is kept for 12 hours at 70° C. The solvent and excess methyl isocyanate are removed and the crude product is chromatographed with ether/hexane (1:3) as eluant, affording the compound of the formula

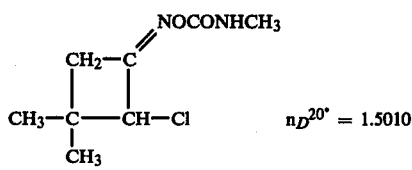

with a refractive index of $n_D^{20} = 1.5188$.

The following compounds are obtained in similar manner:

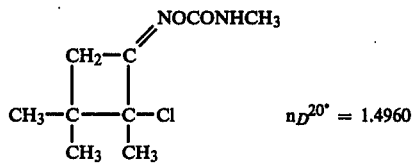

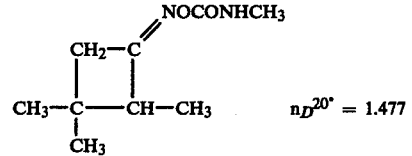

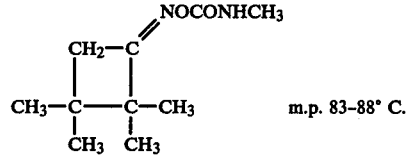

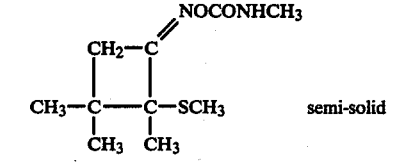

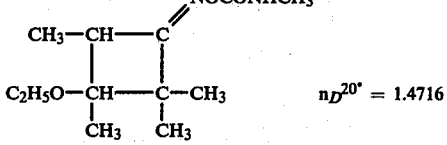

-continued

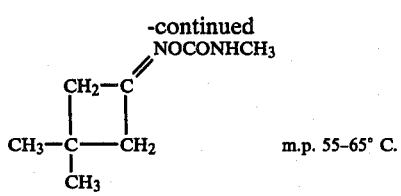

m.p. 55-65° C.

Example 2: Action against *Spodoptera littoralis* and *Heliothis virescens* (larvae and eggs)

Three cotton plants having a height of about 15-20 cm and reared in pots were treated with a sprayable liquid preparation of the compound to be tested. After the spray coating had dried, the potted plants were placed in a metal container having a capacity of about 20 liters and covered with a glass plate. The humidity in the interior of the covered container was regulated such that no water of condensation formed. Direct light falling on the plants was avoided. The three plants were then infested with two egg deposits of *Spodoptera littoralis* or *Heliothis virescens*. Two leaves of each plant were put into a plexiglass cylinder sealed at both ends with muslin. Two egg deposits of Spodoptera or a part of a cotton leaf with eggs of Heliothis deposited thereon were added to the leaves sealed in the cylinder.

Evaluation in comparison to untreated controls was made after 4 to 5 days by determining the hatching rate (number of larvae hatched from the eggs). The compounds of Example 1 exhibited a good ovilarvicidal action in the above test.

Example 3: Systemic insecticidal action against *Aphis fabae*

To determine the systemic action, bean plants (*Vicia fabia*) which had grown roots were put into a 0.01% aqueous solution of active ingredient (obtained from a 10% emulsifiable concentrate). Twenty four hours later, the parts of the plants above the soil were populated with aphids (*Aphis fabae*). By means of a special device the aphids were protected from any possible contact with the test compound either directly or via the gas phase. The test was carried out at 24° C. and 70% relative humidity.

In this test, the compounds of Example 1 exhibited a systemic insecticidal action against *Aphis fabae*.

Example 4: Insecticidal contact action against *Aphis craccivora* and *Mycus persicae*

Before the start of the test, plants (*Vicia faba*) reared in pots were each populated with about 200 insects of the species *Aphis craccivora* or *Myzus persicae*. The treated plants were sprayed 24 hours later dripping wet with a solution containing 200 or 100 ppm of the compound to be tested. Two plants were used for each test compound at its given concentration, and a mortality count was made after a further 24 hours.

In the above test the compounds of Example 1 exhibited a positive action against insects of the species *Aphis craccivora* and *Myzus persicae*.

Example 5: Insecticidal stomach poison and contact action against *Anthonomus grandis*, *Heliothis virescens* and *Spodoptera littoralis*

Cotton plants were sprayed with an aqueous emulsion containing 0.05% of the compound to be tested (obtained from a 25% wettable powder). After the spray coating had dried, the plants were populated with adults and larvae of the species (a) *Anthonomus grandis* (adults)
(b) *Heliothis virescens* (larvae: L3/L4 Instar); or
(c) *Spodoptera littoralis* (larvae: L3 Instar).

Two plants were used for each test compound and test species, and a mortality count was made 2, 4 and 48 hours respectively after the start of the test. The test was carried out at 24° C. and 60% relative humidity.

In the above test the compounds of the formula I were very effective against insects of the above species.

| test compounds | minimum concentration in ppm to achieve 100% kill of | | |
|---|---|---|---|
| | *Aphis craccivora* | *Myzus persicae* | *Spodoptera littoralis* (eggs) |
| CH₃—C(CH₃)(CH₂—C(=NOCONHCH₃))—CH—Cl | 100 | 100 | 200 |
| CH₃—C(CH₃)(CH₂—C(=NOCONHCH₃))—CH—SCH₃ | 200 | 200 | 400 |
| CH₃—C(CH₃)(CH₂—C(=NOCONHCH₃))—C(CH₃)—Cl | 100 | 100 | 200 |

| test compounds | minimum concentration in ppm to achieve 100% kill of | | |
|---|---|---|---|
| | Aphis craccivora | Myzus persicae | Spodoptera littoralis (eggs) |
| 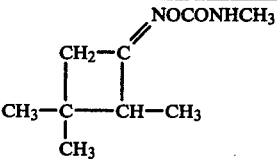 | 200 | 200 | 200 |
| 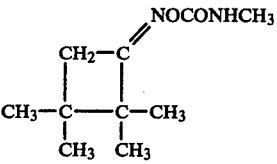 | 200 | 200 | 200 |
| 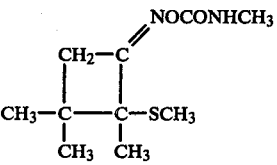 | 200 | 200 | 400 |
| 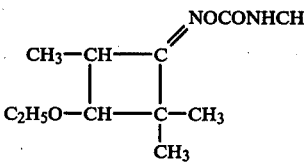 | 100 | 200 | 200 |
| 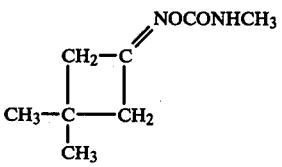 | 100 | 100 | 200 |

What is claimed:

1. A compound of the formula

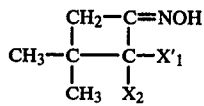

wherein
$X_1'$ is hydrogen, chlorine or methylthio, and
$X_2$ is hydrogen or methyl.

2. The compound according to claim 1 which is 2-chloro-3,3-dimethylcyclobutanone oxime.

3. The compound according to claim 1 which is 2-chloro-2,3,3-trimethylcyclobutanone oxime.

4. The compound according to claim 1 which is 2,3,3-trimethylchlobutanone oxime.

5. The compound according to claim 1 which is 2,3,3-trimethyl-2-methylthiocyclobutanone oxime.

6. The compound according to claim 1 which is 2-methylthio-3,3-dimethylcyclobutanone oxime.

7. The compound 2,2,3,3-tetramethylcyclobutanone oxime.

8. The compound 2,2,4-trimethyl-3-ethoxycyclobutanone oxime.

* * * * *